US012802403B2

(12) United States Patent
Kim et al.

(10) Patent No.: US 12,802,403 B2
(45) Date of Patent: Nov. 17, 2026

(54) METHOD, PROGRAM, AND DEVICE FOR PROCESSING MEDICAL DATA FOR TRAINING OF DEEP LEARNING MODEL

(71) Applicant: AIRS MEDICAL INC., Seoul (KR)

(72) Inventors: Hyeonsoo Kim, Seoul (KR); Joonyoung Yang, Seoul (KR)

(73) Assignee: AIRS MEDICAL INC., Seoul (KR)

( * ) Notice: Subject to any disclaimer, the term of this patent is extended or adjusted under 35 U.S.C. 154(b) by 219 days.

(21) Appl. No.: 18/721,804

(22) PCT Filed: Jun. 20, 2023

(86) PCT No.: PCT/KR2023/008528
§ 371 (c)(1),
(2) Date: Jun. 19, 2024

(87) PCT Pub. No.: WO2023/249372
PCT Pub. Date: Dec. 28, 2023

(65) Prior Publication Data
US 2025/0086942 A1 Mar. 13, 2025

(30) Foreign Application Priority Data
Jun. 22, 2022 (KR) ........................ 10-2022-0076366

(51) Int. Cl.
*G06V 10/77* (2022.01)
*G06N 3/08* (2023.01)
(Continued)

(52) U.S. Cl.
CPC ............... *G06V 10/77* (2022.01); *G06N 3/08* (2013.01); *G06V 10/82* (2022.01); *G16H 30/20* (2018.01);
(Continued)

(58) Field of Classification Search
None
See application file for complete search history.

(56) References Cited

U.S. PATENT DOCUMENTS

2019/0172230 A1 6/2019 Mailhe et al.
2020/0011951 A1 1/2020 Shi et al.
(Continued)

FOREIGN PATENT DOCUMENTS

KR 102199494 B1 1/2021
KR 102328214 B1 11/2021
KR 1020220082302 A 6/2022

OTHER PUBLICATIONS

Sriprabha Ramanarayanan, MAC-ReconNet: A Multiple Acquisition Context based Convolutional Neural Network for MR Image Reconstruction using Dynamic Weight Prediction, Proceedings of Machine Learning Research arXiv, Mar. 10, 2022, pp. 1-13.
(Continued)

*Primary Examiner* — Mark R Milia
(74) *Attorney, Agent, or Firm* — McDonald Hopkins LLC

(57) ABSTRACT

According to an embodiment of the present disclosure, there are disclosed a method, program and device for processing medical data for the training of a deep learning model that is performed by a computing device. The method includes: separating k-space data into a plurality of pieces of different data by taking into consideration characteristics of the metadata of the k-space data; and generating input data and label data for the training of a deep learning model by combining the plurality of pieces of different data separated from the k-space data.

10 Claims, 7 Drawing Sheets

(51) Int. Cl.

| | |
|---|---|
| ***G06V 10/82*** | (2022.01) |
| ***G16H 30/20*** | (2018.01) |
| ***G16H 30/40*** | (2018.01) |
| *G01R 33/561* | (2006.01) |

(52) U.S. Cl.

CPC ......... *G16H 30/40* (2018.01); *G01R 33/5611* (2013.01); *G06V 2201/03* (2022.01); *G06V 2201/10* (2022.01)

(56) References Cited

U.S. PATENT DOCUMENTS

| | | | | |
|---|---|---|---|---|
| 2020/0202586 | A1 | 6/2020 | Li et al. | |
| 2022/0075017 | A1* | 3/2022 | Sabuncu ............ | G01R 33/5608 |
| 2023/0014745 | A1* | 1/2023 | Chen .................... | A61B 5/7267 |
| 2023/0135995 | A1* | 5/2023 | Chen ........................ | G06T 12/30<br>382/131 |
| 2023/0186464 | A1* | 6/2023 | Soliman ................. | A61B 5/055<br>382/128 |

OTHER PUBLICATIONS

Zalan Fabian, et al. Data augmentation for deep learning based accelerated MRI reconstruction with limited data, Proceedings of the 38th International Conference on Machine Learning, PMLR 139, pp. 1-11.
Changheun Oh, et al., A k-space-to-image reconstruction network for MRI using recurrent neural network, Med Phys, Jan. 2021, vol. 48, No. 1, pp. 193-203.
International Search Report for corresponding International Application No. PCT/KR2023/008528 mailed Oct. 4, 2023.
Written Opinion for corresponding International Application No. PCT/KR2023/008528 dated Sep. 27, 2023.

* cited by examiner

[FIG. 1]
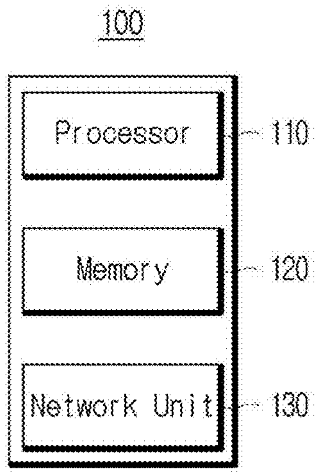

[FIG. 2]
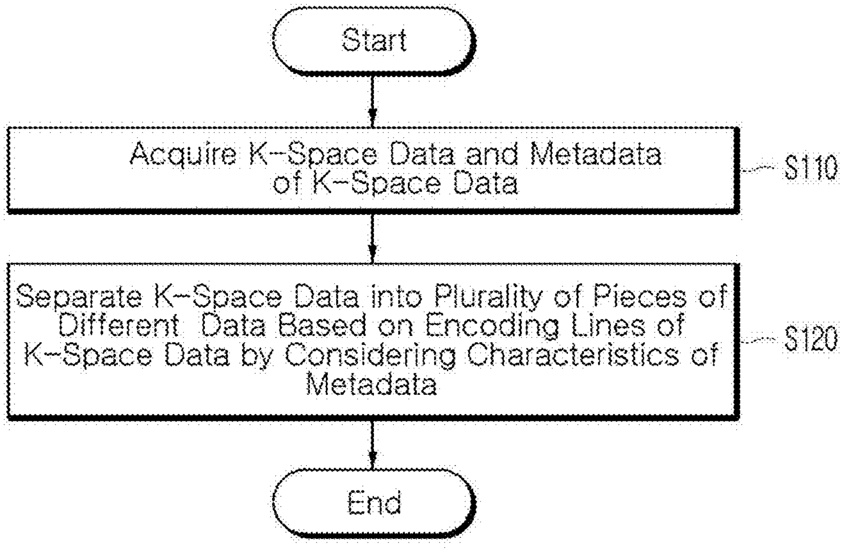

[FIG. 3]
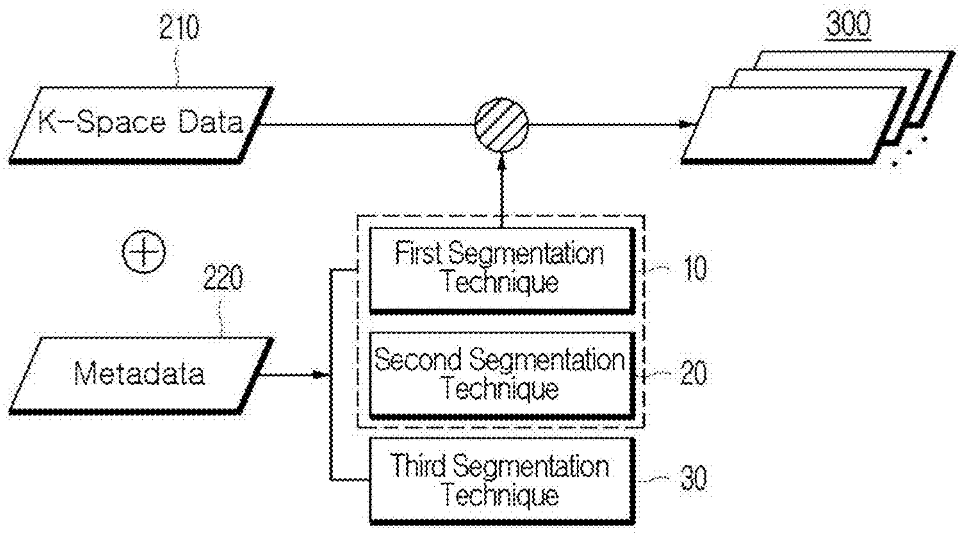

[FIG. 4]
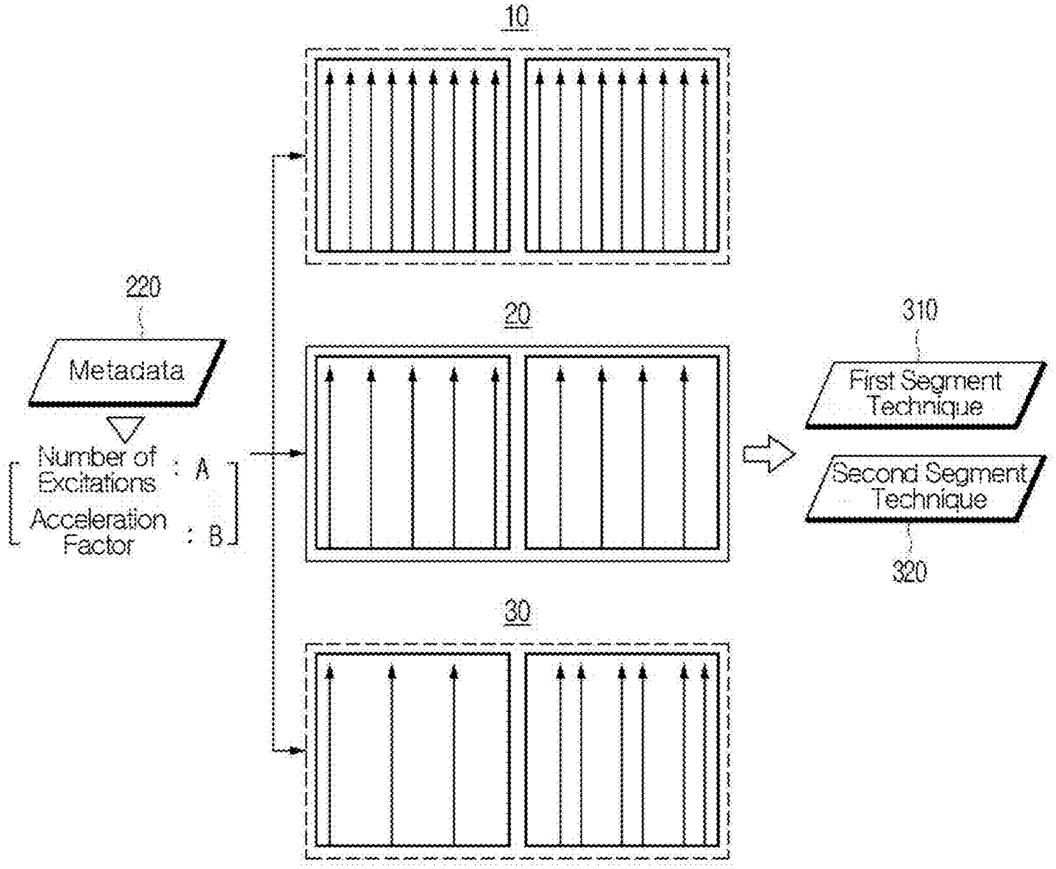

[FIG. 5]
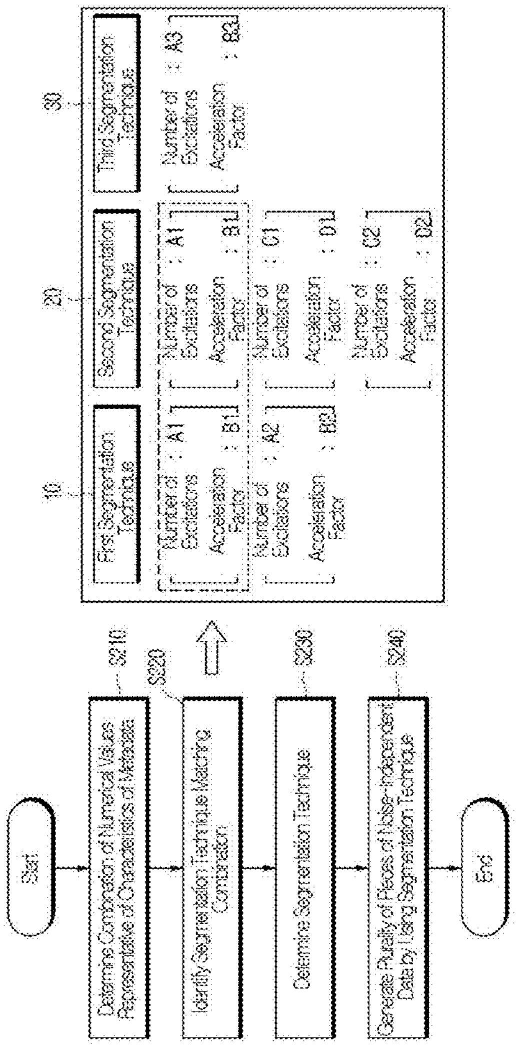

[FIG. 6]
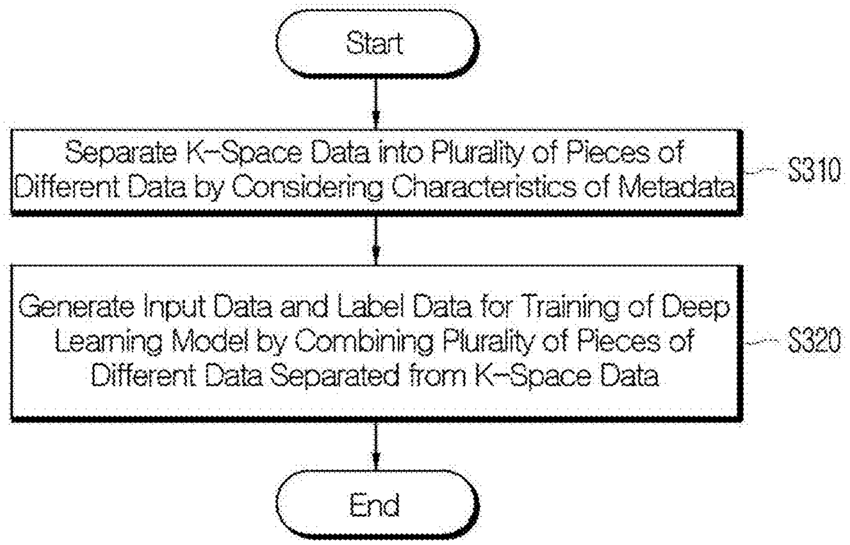
[FIG. 7]
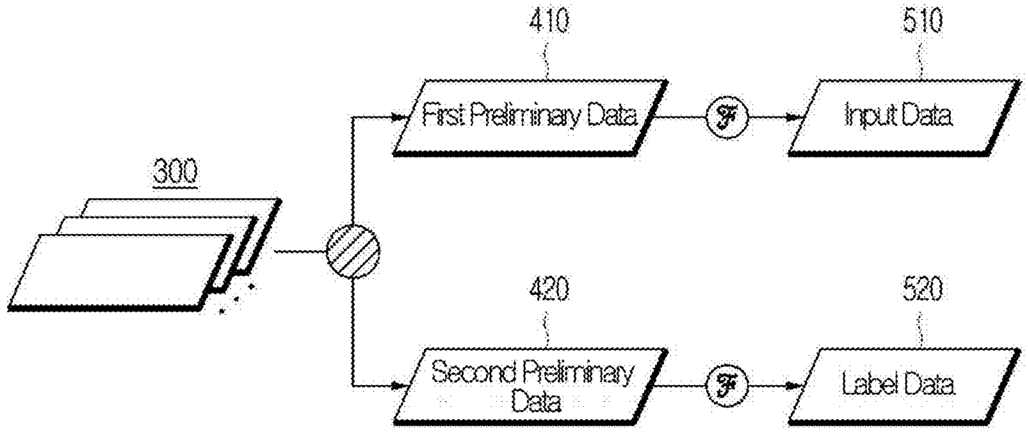

[FIG. 8]
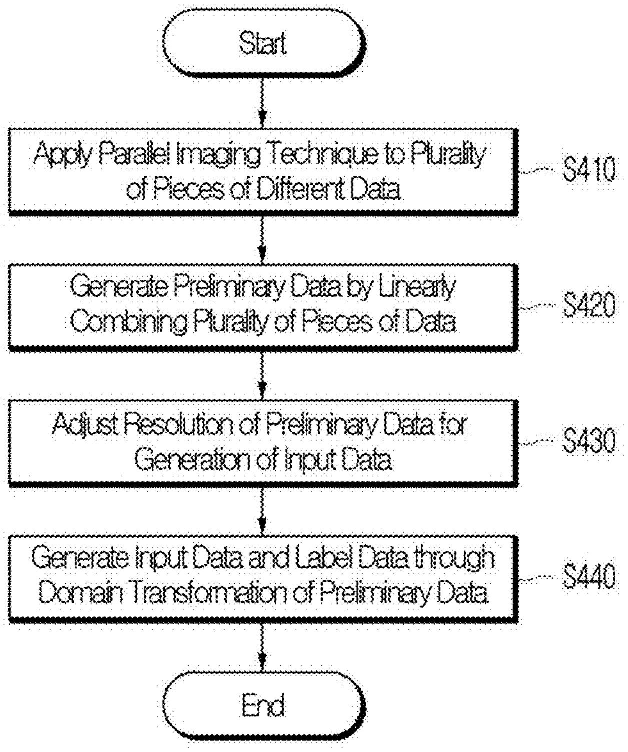

METHOD, PROGRAM, AND DEVICE FOR PROCESSING MEDICAL DATA FOR TRAINING OF DEEP LEARNING MODEL

TECHNICAL FIELD

The present disclosure relates to data processing technology, and more particularly to a method of processing medical data to generate training data for a deep learning model.

BACKGROUND ART

Magnetic resonance imaging (MRI) apparatuses are equipment that requires considerable imaging time. Accordingly, in the medical industry, accelerated imaging technology designed to shorten the imaging time required to take a magnetic resonance image plays a significantly important role and continues to develop. The precondition for the accelerated imaging of a magnetic resonance images is that data is acquired in the signal domain, which is the so-called k-space, rather than the image domain that is observed by humans.

In order for magnetic resonance images acquired through accelerated imaging to be used in the medical field, the magnetic resonance images need to contain all information regarding imaging targets and also the noise affecting the interpretation of the information needs to be minimized. In response to these needs, there has recently been developed the technology that restores low-quality magnetic resonance images acquired through accelerated imaging to a high-quality state unrelated to accelerated imaging based on artificial intelligence. To restore magnetic resonance images acquired through accelerated imaging to high quality based on artificial intelligence, the effective training of an artificial intelligence model needs to be a prerequisite. However, realistic difficulties start to occur in securing data for the training of the artificial intelligence model. For example, to effectively train the artificial intelligence model, not only high-quality input data but also high-quality label data corresponding to the high-quality input data need to be secured. However, even when magnetic resonance images acquired through accelerated imaging are secured as input data to a predetermined extent, there is a problem in that there are virtually no high-quality reconstructed images corresponding to the magnetic resonance images in reality. Therefore, currently, in the industry, it is necessary to secure the training data that is most basically needed to construct the artificial intelligence model.

DISCLOSURE

Technical Problem

The present disclosure has been conceived in response to the above-described background technology, and an object of the present invention is to provide a method of securing high-quality data required for the training of a deep learning model for restoring low-quality medical data to high quality by taking into consideration characteristics of raw medical data.

However, the objects to be accomplished by the present disclosure are not limited to the objects mentioned above, and other objects not mentioned may be clearly understood based on the following description.

Technical Solution

According to an embodiment of the present disclosure for achieving the above-described object, there is disclosed a method of processing medical data for the training of a deep learning model that is performed by a computing device. The method includes: separating k-space data into a plurality of pieces of different data by taking into consideration characteristics of the metadata of the k-space data; and generating input data and label data for the training of a deep learning model by combining the plurality of pieces of different data separated from the k-space data.

Alternatively, the metadata may include at least one of the number of excitations (NEX), the acceleration factor, the parallel imaging technique applied to the k-space data, and the resolution.

Alternatively, generating the input data and the label data for the training of the deep learning model by combining the plurality of pieces of different data separated from the k-space data may include: generating first preliminary data for the generation of the input data and second preliminary data for the generation of the label data by combining the plurality of pieces of data; and generating the input data and the label data by transforming the first preliminary data and the second preliminary data into the image domain.

Alternatively, generating the first preliminary data for the generation of the input data and the second preliminary data for the generation of the label data by combining the plurality of pieces of data may include generating the first preliminary data and the second preliminary data through linear combination that adjusts a noise ratio between the plurality of pieces of data.

Alternatively, the noise of the second preliminary data may include the dependent noise that has a correlation with the noise of the first preliminary data and the independent noise that has no correlation with the noise of the first preliminary data.

Alternatively, in the noise of the second preliminary data, each of the dependent noise and the independent noise may be determined by a coefficient used for linear combination between the plurality of pieces of data.

Alternatively, generating the input data and the label data by transforming the first preliminary data and the second preliminary data into the image domain may include generating the input data and the label data based on Fourier transform for the first preliminary data and the second preliminary data.

Alternatively, generating the input data and the label data by transforming the first preliminary data and the second preliminary data into the image domain may include generating the input data and the label data by inputting the first preliminary data and the second preliminary data to a neural network model.

Alternatively, generating the input data and the label data for the training of the deep learning model by combining the plurality of pieces of different data separated from the k-space data may include adjusting the resolution of the first preliminary data.

Alternatively, adjusting the resolution of the first preliminary data may include adjusting at least one of the basic resolution and phase resolution of the first preliminary data so that the resolution of the first preliminary data has a value smaller than or equal to the resolution of the second preliminary data.

According to an embodiment of the present disclosure for achieving the above-described object, there is disclosed a computer program stored in a computer-readable storage medium. The computer program performs operations of processing medical data for the training of a deep learning model when executed on at least one processor. The operations include operations of: separating k-space data into a plurality of pieces of different data by taking into consideration characteristics of the metadata of the k-space data; and generating input data and label data for the training of a deep learning model by combining the plurality of pieces of different data separated from the k-space data.

According to an embodiment of the present disclosure for achieving the above-described object, there is disclosed a computing device for processing medical data for the training of a deep learning model. The computing device includes: a processor including at least one core; memory including program code executable on the processor; and a network unit configured to acquire k-space data and the meta data of the k-space data. In this case, the processor separates k-space data into a plurality of pieces of different data by taking into consideration characteristics of the metadata of the k-space data, and generates input data and label data for the training of a deep learning model by combining the plurality of pieces of different data separated from the k-space data.

Advantageous Effects

The present disclosure may provide the method of securing high-quality data required for the training of a deep learning model for restoring low-quality medical data to high quality by taking into consideration characteristics of raw medical data.

DESCRIPTION OF DRAWINGS

FIG. 1 is a block diagram of a computing device according to an embodiment of the present disclosure;

FIG. 2 is a flowchart showing a method of processing medical data according to an embodiment of the present disclosure;

FIG. 3 is a conceptual diagram showing a process of processing medical data according to an embodiment of the present disclosure;

FIG. 4 is a conceptual diagram showing a process of segmenting data by taking into consideration characteristics f metadata according to an embodiment of the present disclosure;

FIG. 5 is a flowchart showing a process of segmenting data by taking into consideration characteristics of metadata according to an embodiment of the present disclosure;

FIG. 6 is a flowchart showing a method of processing medical data according to an embodiment of the present disclosure;

FIG. 7 is a conceptual diagram showing a process of processing medical data according to an embodiment of the present disclosure; and FIG. 8 is a flowchart showing a method of generating input data and label data by combining a plurality of pieces of data according to an embodiment of the present disclosure.

MODE FOR INVENTION

Embodiments of the present disclosure will be described in detail below with reference to the accompanying drawings so that those having ordinary skill in the art of the present disclosure (hereinafter referred to as those skilled in the art) can easily implement the present disclosure. The embodiments presented in the present disclosure are provided to enable those skilled in the art to use or practice the content of the present disclosure. Accordingly, various modifications to embodiments of the present disclosure will be apparent to those skilled in the art. That is, the present disclosure may be implemented in various different forms and is not limited to the following embodiments.

The same or similar reference numerals denote the same or similar components throughout the specification of the present disclosure. Additionally, in order to clearly describe the present disclosure, reference numerals for parts that are not related to the description of the present disclosure may be omitted in the drawings.

The term “or” used herein is intended not to mean an exclusive “or” but to mean an inclusive “or.” That is, unless otherwise specified herein or the meaning is not clear from the context, the clause “X uses A or B” should be understood to mean one of the natural inclusive substitutions. For example, unless otherwise specified herein or the meaning is not clear from the context, the clause “X uses A or B” may be interpreted as any one of a case where X uses A, a case where X uses B, and a case where X uses both A and B.

The term “and/or” used herein should be understood to refer to and include all possible combinations of one or more of listed related concepts.

The terms “include” and/or “including” used herein should be understood to mean that specific features and/or components are present. However, the terms “include” and/or “including” should be understood as not excluding the presence or addition of one or more other features, one or more other components, and/or combinations thereof.

Unless otherwise specified herein or unless the context clearly indicates a singular form, the singular form should generally be construed to include “one or more.”

The term “N-th (N is a natural number)” used herein can be understood as an expression used to distinguish the components of the present disclosure according to a predetermined criterion such as a functional perspective, a structural perspective, or the convenience of description. For example, in the present disclosure, components performing different functional roles may be distinguished as a first component or a second component. However, components that are substantially the same within the technical spirit of the present disclosure but should be distinguished for the convenience of description may also be distinguished as a first component or a second component.

Meanwhile, the term “module” or “unit” used herein may be understood as a term referring to an independent functional unit processing computing resources, such as a computer-related entity, firmware, software or part thereof, hardware or part thereof, or a combination of software and hardware. In this case, the “module” or “unit” may be a unit composed of a single component, or may be a unit expressed as a combination or set of multiple components. For example, in the narrow sense, the term “module” or “unit” may refer to a hardware component or set of components of a computing device, an application program performing a specific function of software, a procedure implemented through the execution of software, a set of instructions for the execution of a program, or the like. Additionally, in the broad sense, the term “module” or “unit” may refer to a computing device itself constituting part of a system, an application running on the computing device, or the like. However, the above-described concepts are only examples, and the concept of “module” or “unit” may be defined in various manners within a range understandable to those skilled in the art based on the content of the present disclosure.

The term “model” used herein may be understood as a system implemented using mathematical concepts and language to solve a specific problem, a set of software units intended to solve a specific problem, or an abstract model for a process intended to solve a specific problem. For example, a neural network "model" may refer to an overall system implemented as a neural network that is provided with problem-solving capabilities through training. In this case, the neural network may be provided with problem-solving capabilities by optimizing parameters connecting nodes or neurons through training. The neural network "model" may include a single neural network, or a neural network set in which multiple neural networks are combined together.

"Data" used herein may include an "image." The term "image" used herein may refer to multidimensional data composed of discrete image elements. In other words, "image" may be understood as a term referring to a digital representation of an object that can be seen by the human eye. For example, "image" may refer to multidimensional data composed of elements corresponding to pixels in a two-dimensional image. "Image" may refer to multidimensional data composed of elements corresponding to voxels in a three-dimensional image.

The term "medical image archiving and communication system (PACS)" used herein refers to a system that stores, processes, and transmits medical images in accordance with the Digital Imaging and Communications in Medicine (DICOM) standard. For example, the "PACS" operates in conjunction with digital medical imaging equipment, and stores medical images such as magnetic resonance imaging (MRI) images and computed tomography (CT) images in accordance with the DICOM standard. The "PACS" transmit medical images to terminals inside and outside a hospital over a communication network. In this case, meta information such as reading results and medical records may be added to the medical images.

The term "k-space" used herein may be understood as an array of numbers representing the spatial frequencies of a magnetic resonance image. In other words, the "k-space" may be understood as a frequency space corresponding to a three-dimensional space corresponding to coordinates of a magnetic resonance space.

The term "Fourier transform" used herein may be understood as an operation medium that enables the description of the correlation between the time domain and the frequency domain. In other words, "Fourier transform" used herein may be understood as a broad concept representing an operation process for the mutual transformation between the time domain and the frequency domain. Accordingly, the "Fourier transform" used herein may be understood as a concept that encompasses both the Fourier transform in a narrow sense, which decomposes a signal in the time domain into the frequency domain, and inverse Fourier transform, which transforms a signal in the frequency domain into the time domain.

The foregoing descriptions of the terms are intended to help to understand the present disclosure. Accordingly, it should be noted that unless the above-described terms are explicitly described as limiting the content of the present disclosure, the terms in the content of the present disclosure are not used in the sense of limiting the technical spirit of the present disclosure.

FIG. 1 is a block diagram of a computing device according to an embodiment of the present disclosure.

A computing device 100 according to an embodiment of the present disclosure may be a hardware device or part of a hardware device that performs the comprehensive processing and calculation of data, or may be a software-based computing environment that is connected to a communication network. For example, the computing device 100 may be a server that performs an intensive data processing function and shares resources, or may be a client that shares resources through interaction with a server. Furthermore, the computing device 100 may be a cloud system in which a plurality of servers and clients interact with each other and comprehensively process data. Since the above descriptions are only examples related to the type of computing device 100, the type of computing device 100 may be configured in various manners within a range understandable to those skilled in the art based on the content of the present disclosure.

Referring to FIG. 1, the computing device 100 according to an embodiment of the present disclosure may include a processor 110, memory 120, and a network unit 130. However, FIG. 1 shows only an example, and the computing device 100 may include other components for implementing a computing environment. Furthermore, only some of the components disclosed above may be included in the computing device 100.

The processor 110 according to an embodiment of the present disclosure may be understood as a configuration unit including hardware and/or software for performing computing operation. For example, the processor 110 may read a computer program and perform data processing for machine learning. The processor 110 may process computational processes such as the processing of input data for machine learning, the extraction of features for machine learning, and the calculation of errors based on backpropagation. The processor 110 for performing such data processing may include a central processing unit (CPU), a general purpose graphics processing unit (GPGPU), a tensor processing unit (TPU), an application specific integrated circuit (ASIC), or a field programmable gate array (FPGA). Since the types of processor 110 described above are only examples, the type of processor 110 may be configured in various manners within a range understandable to those skilled in the art based on the content of the present disclosure.

The processor 110 may generate training data for a deep learning model to restore low-quality medical data to high quality. The processor 110 may generate input data and label data for the training of the deep learning model by using metadata associated with medical data. The processor 110 may generate input data and label data for the training of the deep learning model from medical data by taking into consideration the characteristics of the metadata of the medical data. In this case, the medical data may include a magnetic resonance signal or image obtained through accelerated imaging or accelerated simulation. Furthermore, the deep learning model may include a neural network model that restores a magnetic resonance image obtained through accelerated imaging or accelerated simulation to a normal imaging condition. In other words, the deep learning model may include a neural network model that generates output intended to reduce the noise of a magnetic resonance image obtained through accelerated imaging or accelerated simulation or improve the resolution thereof. For example, the neural network model may include U-NET, which is based n a convolutional neural network. Since the above-described type of neural network is only an example, it may be configured in various manners within a range understandable to those skilled in the field of computer vision.

Meanwhile, in the present disclosure, the accelerated imaging may be understood as an imaging technique that shortens imaging time by reducing the number of excitations (NEX) for a magnetic resonance signal compared to general imaging. The number of excitations may be understood as the number of repetitions when lines of a magnetic resonance signal are repeatedly acquired in the k-space domain. Accordingly, as the number of excitations increases, the imaging time required to image a magnetic resonance image may increase proportionally. That is, in the case where the number of excitations decreases when a magnetic resonance image is imaged, the accelerated imaging for which the imaging time required to image a magnetic resonance image is shortened may be implemented.

In the present disclosure, the accelerated imaging may be understood as an imaging technique that shortens imaging time by increasing the acceleration factor compared to regular imaging. The acceleration factor is a term used in a parallel imaging technique, and may be understood as a value obtained by dividing the number of signal lines fully sampled in the K-space domain by the number of signal lines sampled through imaging. For example, an acceleration factor of 2 can be understood as obtaining a number of signal lines equivalent to half of the number of fully sampled signal lines when lines are obtained by sampling a magnetic resonance signal in the phase encoding direction. Accordingly, as the acceleration factor increases, the imaging time of a magnetic resonance image may decrease proportionally. That is, when the acceleration factor is increased during the imaging of a magnetic resonance image, accelerated imaging in which magnetic resonance image imaging time is shortened may be implemented.

In the present disclosure, the accelerated imaging may be understood as an imaging technique that shortens imaging time by increasing the acceleration factor compared to regular imaging. The acceleration factor is a term used in parallel imaging techniques, and may be understood as a value obtained by dividing the number of signal lines fully sampled in k-space by the number of signal lines sampled through imaging. For example, the fact that the acceleration factor is 2 may be understood as obtaining a number of signal lines equal to half of the number of fully sampled signal lines when obtaining lines by sampling a magnetic resonance signal in the phase encoding direction. Accordingly, as the acceleration factor increases, the imaging time required to image a magnetic resonance image may decrease proportionally. That is, in the case where the acceleration factor increases when a magnetic resonance image is imaged, the accelerated imaging in which the imaging time required to image a magnetic resonance image is shortened may be implemented.

In the present disclosure, the accelerated imaging may be understood as an imaging technique that generates a magnetic resonance image by acquiring a sub-sampled magnetic resonance signal. In this case, the subsampling may be understood as an operation of sampling a magnetic resonance signal at a sampling rate lower than the Nyquist sampling rate. Accordingly, the medical data of the present disclosure may be an image acquired by sampling a magnetic resonance signal at a sampling rate lower than the Nyquist sampling rate.

The accelerated simulation of the present disclosure may be understood as an operation technique for under-sampling k-space data generated through regular or accelerated imaging. In this case, the under-sampling may be understood as a method of processing a magnetic resonance signal at a lower sampling rate based on the k-space data to be processed. For example, the accelerated simulation may include an operation technique that generates subsampled k-space data based on fully sampled k-space data. Furthermore, the accelerated simulation may include an operation technique that samples a magnetic resonance signal at a lower sampling rate based on subsampled k-space data. In addition to these examples, the accelerated imaging technique described above may be applied to the accelerated simulation without change. The acceleration simulation may be performed by the processor 110 of the present disclosure, or may be performed through a separate external system.

However, since the above description of accelerated imaging or accelerated simulation is only an example, the concept of accelerated imaging may be defined in various manners within a range understandable to those skilled in the art based on the content of the present disclosure.

The processor 110 may separate k-space data into a plurality of pieces of different data based on the metadata of the k-space data. The processor 110 may segment k-space data into a plurality of pieces of different data based on the encoding lines of the k-space data by analyzing the metadata of the k-space data. The processor 110 may generate a plurality of pieces of different data, distinguished based on encoding lines, from k-space data by taking into consideration the characteristics of the metadata of the k-space data. In this case, the k-space data may correspond to a magnetic resonance signal or image in the k-space domain that has been subjected to accelerated imaging or accelerated simulation.

The processor 110 may determine the characteristics that the metadata of k-space data has. Furthermore, the processor 110 may select an appropriate segmentation technique based on the results of the above-described determination, and may generate a plurality of pieces of different data from the k-space data. In other words, the processor 110 may identify a segmentation technique for separating the k-space data into a plurality of pieces of different data according to the characteristics of the metadata of k-space data. Furthermore, the processor 110 may generate a plurality of pieces of different data from k-space data by using a previously identified segmentation technique. For example, the processor 110 may select a segmentation technique, matching the characteristics of the metadata of the k-space data currently being processed, from among segmentation techniques previously classified according to the characteristics of metadata. In this case, the metadata may include at least one of the number of excitations, the acceleration factor, the parallel imaging technique applied to the k-space data, and the resolution. The processor 110 may generate a plurality of pieces of different data, distinguished based on encoding lines, from k-space data by using the segmentation technique that matches the characteristics of the metadata of the k-space data currently being processed.

In other words, the processor 110 may route an appropriate segmentation technique suitable for characteristics of k-space data by taking into consideration the acceleration characteristics that the K-space data has. Through such routing and data processing, the processor 110 may prepare basic data for generating input data and label data optimized for the training of the deep learning model from the k-space data.

The processor 110 may generate training data for the deep learning model based on the plurality of pieces of different data generated from the k-space data. The processor 110 may generate input data and label data for the training of the deep learning model by combining the plurality of pieces of different data separated from the k-space data. For example, the processor 110 may generate preliminary data intended to prepare input data for the training of the deep learning model by combining the plurality of pieces of different data. Furthermore, the processor 110 may generate preliminary data intended to prepare label data by combining the plurality of pieces of different data. In this case, to allow the label data to have a difference in noise or resolution from the input data, the processor 110 may individually perform an operation for generating preliminary data for the input data and an operation for generating preliminary data for the label data by taking into consideration the combination ratio between the plurality of pieces of data. The processor 110 may generate input data and label data for the training of the deep learning model based on respective pieces of preliminary data.

That is, the processor 110 may generate input data for the training of the deep learning model and high-quality label data corresponding to the input data from single k-space data by taking into consideration the inherent characteristics of the k-space data. Through this data processing process, the processor 110 may effectively construct training data for the deep learning model for restoring a magnetic resonance image acquired through accelerated imaging or accelerated simulation.

The memory 120 according to an embodiment of the present disclosure may be understood as a configuration unit including hardware and/or software for storing and managing data that is processed in the computing device 100. That is, the memory 120 may store any type of data generated or determined by the processor 110 and any type of data received by the network unit 130. For example, the memory 120 may include at least one type of storage medium of a flash memory type, hard disk type, multimedia card micro type, and card type memory, random access memory (RAM), static random access memory (SRAM), read-only memory (ROM), electrically erasable programmable read-only memory (EEPROM), programmable read-only memory (PROM), magnetic memory, a magnetic disk, and an optical disk. Furthermore, the memory 120 may include a database system that controls and manages data in a predetermined system. Since the types of memory 120 described above are only examples, the type of memory 120 may be configured in various manners within a range understandable to those skilled in the art based on the content of the present disclosure.

The memory 120 may structure, organize, and manage data necessary for the processor 110 to perform computation, the combination of data, and program codes executable on the processor 110. For example, the memory 120 may store medical data received through the network unit 130, which will be described later. The memory 120 may store program code configured to perform operation so that medical data is processed to generate training data for a neural network model, program code configured to operate the processor 110 to generate image data based on the feature interpretation (or feature inference) of the neural network model, and k-space data, image data, etc. generated as the program code is executed.

The network unit 130 according to an embodiment of the present disclosure may be understood as a configuration unit that transmits and receives data through any type of known wired/wireless communication system. For example, the network unit 130 may perform data transmission and reception using a wired/wireless communication system such as a local area network (LAN), a wideband code division multiple access (WCDMA) network, a long term evolution (LTE) network, the wireless broadband Internet (WiBro), a 5th generation mobile communication (5G) network, a ultra wide-band wireless communication network, a ZigBee network, a radio frequency (RF) communication network, a wireless LAN, a wireless fidelity network, a near field communication (NFC) network, or a Bluetooth network. Since the above-described communication systems are only examples, the wired/wireless communication system for the data transmission and reception of the network unit 130 may be applied in various manners other than the above-described examples.

The network unit 130 may receive data necessary for the processor 110 to perform computation through wired/wireless communication with any system or client or the like. Furthermore, the network unit 130 may transmit data generated through the computation of the processor 110 through wired/wireless communication with any system or client or the like. For example, the network unit 130 may receive medical data through communication with a PACS, a cloud server that performs tasks such as the standardization of medical data, or a computing device. The network unit 130 may transmit training data generated through the operations of the processor 110, image data corresponding to the output of the neural network model, etc. through communication with the above-described PACS, cloud server, or computing device.

FIG. 2 is a flowchart showing a method of processing medical data according to an embodiment of the present disclosure.

Referring to FIG. 2, the computing device 100 according to an embodiment of the present disclosure may acquire k-space data and the metadata of the k-space data in step S110. In this case, the term "acquisition" may be understood to mean not only receiving data over a wireless communication network connecting with an external terminal, device or system, but also generating or receiving data in an on-device form. For example, the computing device 100 may receive k-space data and the metadata of the k-space data through cloud communication with a PACS or a magnetic resonance imaging apparatus. The computing device 100 may be mounted on a magnetic resonance imaging apparatus and directly acquire k-space data and the metadata of the k-space data. In this case, the metadata of the k-space data may be metadata related to the accelerated imaging of the k-space data. The metadata of the k-space data may include at least one of the number of excitations, the acceleration factor, the parallel imaging technique applied to the k-space data, and the resolution.

In step S120, the computing device 100 may separate the k-space data into a plurality of pieces of different data based on the encoding lines of the k-space data by taking consideration the characteristics of the metadata acquired through step S110. The computing device 100 may generate a plurality of pieces of data, distinguished from each other based on encoding lines, from the k-space data by analyzing numerical values representing the characteristics of the metadata. For example, the computing device 100 may identify a segmentation technique appropriate for application to the k-space data, obtained through step S110, based on at least one numerical value of the number of excitations, the acceleration factor, the parallel imaging technique, and the resolution. In this case, the identification may be understood as a task of selecting an appropriate segmentation technique from among the segmentation techniques pre-classified in accordance with the combination of at least one numerical value of the number of excitations, the acceleration factor, the parallel imaging technique, and the resolution. The computing device 100 may generate a plurality of pieces of data, distinguished from each other based on encoding lines, from the k-space data by using the identified segmentation technique. In this case, the plurality of pieces of data may be understood as basic data used to generate input data and label data for the training of the deep learning model.

FIG. 3 is a conceptual diagram showing a process of processing medical data according to an embodiment of the present disclosure. Furthermore, FIG. 4 is a conceptual diagram showing a process of segmenting data by taking into consideration characteristics of metadata according to an embodiment of the present disclosure.

Referring to FIG. 3, the processor 110 of the computing device 100 according to an embodiment of the present disclosure may generate a plurality of pieces of data 300 to be used to prepare training data for a deep learning model for the restoration of medical data based on k-space data 210 and the metadata 220 of the k-space data 210. The processor 110 may identify a segmentation technique for separating the k-space data 210 into the plurality of pieces of different data 300 based on the characteristics of the metadata 220. In this case, the characteristics of the metadata 220 may be parameters related to the accelerated imaging of the k-space data 210, or attribute values indicating an accelerated imaging or restoration technique. The processor 110 may generate a plurality of pieces of data 300, independent of each other in terms of noise, from the k-space data 210 based on the encoding lines by using the identified segmentation technique. In this case, the encoding lines may be understood as a frequency or phase encoding set that forms the dimension of the k-space data.

For example, the processor 110 may determine the combination of numerical values representing the characteristics of the metadata 220. The processor 110 may determine a segmentation technique matching the combination to be a segmentation technique used to generate a plurality of pieces of data 300 that are independent of each other in terms of noise. The processor 110 may select a segmentation technique matching the combination of numerical values from among the segmentation techniques pre-classified based on the combination of numerical values representing the characteristics of the metadata 200. That is, the processor 110 may appropriately use a segmentation technique appropriate for the k-space data by individually taking into consideration how the k-space data was imaged. In other words, the processor 110 may determine a segmentation technique suitable for the k-space data by taking into consideration the characteristics of metadata for the k-space data that can be used as a clinical standard. This data processing process ensures that even when any type of k-space data is acquired, high-quality data independent in terms of noise may be acquired through a technique optimized for the k-space data itself.

According to an embodiment of the present disclosure, the segmentation technique may include a first segmentation technique 10 that generates a plurality of pieces of data, mutually independent of each other in terms of noise, from k-space data based on the order of accelerated imaging according to the number of excitations. Furthermore, the segmentation technique may include a second segmentation technique 20 that generates a plurality of pieces of data mutually, independent of each other in terms of noise, from k-space data based on the interval between phase encoding lines. For example, the first segmentation technique 10 may include a technique that determines whether data in question is first or second imaged data according to the number of excitations and generate a plurality of pieces of data by segmenting k-space data according to the order of imaging. The second segmentation technique 20 may include a segmentation technique that distinguishes the phase encoding lines of k-space data by setting the interval between the phase encoding lines to 2 and generates a plurality of pieces of data, mutually independent of each other in terms of noise, from the k-space data based on the distinguished phase encoding lines. That is, the second segmentation technique 20 may include a technique that determines whether each of phase encoding lines is odd or even and generates a plurality of pieces of data by segmenting the k-space data according to this pattern. In addition to the above-described example where the interval between phase encoding lines is 2, the second segmentation technique 20 may also include a case where the interval between phase encoding lines is 2 or more. In other words, the second segmentation technique 20 may include a segmentation technique that distinguishes the phase encoding lines of k-space data by setting the interval between the phase encoding lines to n (n is a natural number larger than 2) and generates a plurality of pieces of data, mutually independent of each other in terms of noise, from the k-space data based on the distinguished phase encoding lines.

The first segmentation technique 10 and second segmentation technique 20 described above may be classified in advance by being matched with individual combinations of numerical values representing the characteristics of metadata. Accordingly, the processor 110 may determine at least one of the pre-classified first segmentation technique 10 or the second segmentation technique 20 based on a combination of numerical values representing the characteristics of the metadata 220 to be a segmentation technique used to generate a plurality of pieces of data 300 that are mutually independent of each other in terms of noise. More specifically, referring to FIG. 4, when the combination of numerical values representing the characteristics of the metadata 220 is [number of excitations A, acceleration factor B], the processor 110 may determine the first segmentation technique 10, which belongs to the segmentation techniques 21 and 22 included in the first segmentation technique 10 or the second segmentation technique 20 and matches [number of excitations A, acceleration factor B], to be a segmentation technique for segmenting the k-space data 210. In this case, the 2-1 segmentation technique 21 included in the second segmentation technique 20 may correspond to a segmentation technique in which the interval between phase encoding lines is 2. The 2-2 segmentation technique 22 included in the second segmentation technique 20 may correspond to a segmentation technique in which the interval between phase encoding lines is 3.

Meanwhile, since the types of segmentation technique described above are only examples, the segmentation technique may be additionally defined in a range understandable to those skilled in the art based on the content of the present disclosure in addition to the above-described examples.

The processor 110 may generate a plurality of pieces of data 300, mutually independent of each other in terms of noise, from the k-space data 210 based on the encoding lines by using at least one of the pre-classified segmentation techniques. For example, referring to FIG. 4, according to the combination of numerical values representing the characteristics of the metadata 220, the processor 110 may generate first segment data 310 and second segment data 320 by segmenting the k-space data 210 into two by using the first segmentation technique 10. In this case, the first segment data 310 and the second segment data 320 correspond to each other in terms of signal intensity, but may be different from and be independent of each other in terms of at least one of noise intensity and distribution. When the noise of the first segment data 310 and the second segment data 320 are independent of each other as described above, input data and label data suitable for the training of the deep learning model that alleviates noise to restore medical data may be effectively generated by combining the first segment data 310 and the second segment data 320. That is, the processor 110 may generate the plurality of pieces of data 300, independent of each other in terms of at least one of the intensity and distribution of noise, from the k-space data 210 through a segmentation technique matching the characteristics of the metadata 220, so that it may be possible to efficiently construct a high-quality data set that serves as the basis for generating input data and label data, which will be described later.

FIG. 5 is a flowchart showing a process of segmenting data by taking into consideration characteristics of metadata according to an embodiment of the present disclosure. Details matching descriptions of FIGS. 3 and 4 for each step of FIG. 5 will be omitted.

Referring to FIG. 5, the processor 110 of the computing device 100 according to an embodiment of the present disclosure may determine a combination of numerical values representing characteristics of metadata in step S210. Furthermore, the processor 110 may identify a segmentation technique matching the combination among previously classified segmentation techniques in step S220. For example, as shown in FIG. 5, the first segmentation technique 10 and the second segmentation technique 20 may be previously classified according to combinations of numerical values representing characteristics of metadata. In this case, when the combination of characteristic values of metadata to be processed is [number of excitations A1, acceleration factor B1], the processor 110 may determine at least one of the first segmentation technique 10 and the second segmentation technique 20 matching [number of excitations A1, acceleration factor B1] to be a segmentation technique to be applied to a processing target.

The processor 110 may determine the segmentation technique identified in step S220 to be a segmentation technique to be used to separate a plurality of pieces of data from the k-space data in step S230. Then, the processor 110 may generate a plurality of pieces of data, independent of each other in terms of noise, by using the determined segmentation technique in step S240.

FIG. 6 is a flowchart showing a method of processing medical data according to an embodiment of the present disclosure.

Referring to FIG. 6, the computing device 100 according to an embodiment of the present disclosure may separate the k-space data into a plurality of pieces of different data by taking into consideration the characteristics of the metadata of the k-space data in step S310. Since details related to step S310 match those of step S120 of FIG. 2 described above, detailed description will be omitted.

The computing device 100 may generate input data and label data for the training of the deep learning model by combining the plurality of pieces of different data separated from the k-space data in step S320. In this case, the plurality of pieces of different data may be understood as a plurality of pieces of data that are independent of each other in terms of at least one of the intensity and distribution of noise. The computing device 100 may prepare preliminary data to be used to generate input data and label data for the training of the deep learning model by combining the plurality of pieces of different data. The computing device 100 may generate input data and label data to be used for the training of the deep learning model by transforming the preliminary data into the image domain. That is, the computing device 100 may prepare preliminary data for generating input data and label data for the training of the deep learning model by using the basic data prepared through step S310, and may generate input data and label data through the domain transformation of the preliminary data.

FIG. 7 is a conceptual diagram showing a process of processing medical data according to an embodiment of the present disclosure.

Referring to FIG. 7, the processor 110 of the computing device 100 according to an embodiment of the present disclosure may generate first preliminary data 410 for generating the input data 510 and second preliminary data 420 for generating the label data 520 by combining the plurality of pieces of data 300 that are mutually independent of each other in terms of noise. For example, the processor 110 may generate first preliminary data 410 for the generation of the input data 510 and second preliminary data 420 for the generation of the label data 520 through the linear combination that adjusts the noise ratio between multiple pieces of data. More specifically, it is assumed that through a processing process such as that shown in the example of FIG. 4, two pieces of data that have the same signal intensity but are independent of each other in terms of the intensity and distribution of noise. The processor 110 may generate the first preliminary data 410 by linearly combining the two pieces of data by applying a linear combination coefficient of 1 to one of the two data and a linear combination coefficient of 0 to the other one. That is, the first preliminary data 410 may correspond to data to which a linear combination coefficient of 1 has been applied. The processor 110 may generate the second preliminary data 420 by linearly combining the two pieces of data through the application of a linear combination coefficient of ⅓ to the data corresponding to the first preliminary data 410 and a linear combination coefficient of ⅔ to the remaining data. That is, the second preliminary data 420 may be generated as data including noise that has been reduced to ⅓ of the noise of the first preliminary data 410. Through linear combination such as that shown in the above-described example, the processor 110 may generate the preliminary data 410 and 420 whose noise ratio has been variously adjusted according to a linear combination coefficient to be individually suitable for the purpose of generating the input data 510 or label data 520 based on the plurality of pieces of data 300 that are independent of each other in terms of noise.

Meanwhile, according to the above-described example, the noise of the second preliminary data 420 may include the dependent noise that has a correlation with the noise of the first preliminary data 410 and the independent noise that has no correlation with the noise of the first preliminary data 410. More specifically, the dependent noise may correspond to the noise obtained by applying a linear combination coefficient of ⅓ to the noise of data corresponding to the first preliminary data 410 of the plurality of pieces of data. Furthermore, the independent noise may correspond to the noise obtained by applying a linear combination coefficient of ⅔ to the noise of the remaining data that does not correspond to the first preliminary data 410. The ratio of linear combination coefficients in the preceding examples is only an example, and the ratio of linear combination coefficients may be adjusted in various manners to suit the purpose of generating input data and label data.

The processor 110 may generate the input data 510 and the label data 520 by transforming the first preliminary data 410 and the second preliminary data 420 into the image domain. For example, the processor 110 may generate the input data 510 and the label data 520 based on Fourier transform for the first preliminary data 410 and the second preliminary data 420. The processor 110 may generate the input data 510 and the label data 520 by inputting the first preliminary data 410 and the second preliminary data 420 into a neural network model that transforms the k-space domain into the image domain. The data processing process described through FIG. 7 may allow high-quality data required for each purpose of generating input or label for the training of the deep learning model to be generated rapidly and accurately as desired by utilizing pieces of data that are mutually independent of each other in terms of noise.

FIG. 8 is a flowchart showing a method of generating input data and label data by combining a plurality of pieces of data according to an embodiment of the present disclosure. Details matching descriptions of FIG. 7 for each step of FIG. 8 will be omitted.

Referring to FIG. 8, the computing device 100 according to an embodiment of the present disclosure may apply a parallel imaging technique to a plurality of pieces of different data that are mutually independent of each other in terms of noise in step S410. The parallel imaging technique may be understood as an image processing technique for restoring information the missing of a magnetic resonance image acquired through accelerated imaging. For example, the computing device 100 may restore a plurality of pieces of data by reconstructing autocalibrating signal (ACS) lines of a plurality of pieces of different data. The computing device 100 may restore a plurality of pieces of data by reconstructing magnetic resonance signal lines that constitute a plurality of pieces of different data. Furthermore, the computing device 100 may restore a plurality of pieces of data by using a sensitivity map based on sensitivity information for each channel of coils used to acquire k-space data. In addition to the above-described examples, various parallel imaging techniques may be applied within a range understandable to those skilled in the art based on the content of the present disclosure. When the plurality of pieces of data are the data restored through a parallel imaging technique, step S410 may not be performed.

The processor 110 may generate preliminary data for generating training data for the deep learning model that restores the quality of medical data by linearly combining a plurality of pieces of data that are mutually independent of each other in terms of noise in step S420. In this case, the plurality of pieces of data may be understood as data restored through a parallel imaging technique.

The processor 110 may adjust the resolution of preliminary data for the generation of input data to be used for the training of the deep learning model in step S430. For example, the processor 110 may perform at least one of the basic resolution or phase resolution 4 the first preliminary data such that the resolution of the first preliminary data related to the input data has a value smaller than or equal to the resolution of the second preliminary data related to the label data. In this case, the basic resolution is the number of pixels in the readout direction, and may be understood as the relative size of data present in the frequency encoding direction. Furthermore, the phase resolution is the number of pixels in the phase encoding direction, and may be understood as the relative size of data present in the phase encoding direction. The range in which the resolution is adjusted may be determined according to a value preset by a user. Therefore, the resolution of the input data to be used for the training of the deep learning model may be adjusted in various manners within a range lower than the resolution of the label data.

In step S440, the processor 110 may generate input data and label data by transforming the domain of the preliminary data whose resolution has been adjusted through step S430. Furthermore, the processor 110 may use the input data and the label data as training data for the deep learning model for restoring the quality of medical data.

The various embodiments of the present disclosure described above may be combined with one or more additional embodiments, and may be changed within the range understandable to those skilled in the art in light of the above detailed description. The embodiments of the present disclosure should be understood as illustrative but not restrictive in all respects. For example, individual components described as unitary may be implemented in a distributed manner, and similarly, the components described as distributed may also be implemented in a combined form. Accordingly, all changes or modifications derived from the meanings and scopes of the claims of the present disclosure and their equivalents should be construed as being included in the scope of the present disclosure.

The invention claimed is:

1. A method of processing medical data for training of a deep learning model, the method being performed by a computing device including at least one processor, the method comprising:

separating k-space data into a plurality of pieces of different data by taking into consideration characteristics of metadata of the k-space data; and generating input data and label data for training of a deep learning model by combining the plurality of pieces of different data separated from the k-space data, wherein generating the input data and the label data for the training of the deep learning model by combining the plurality of pieces of different data separated from the k-space data comprises:

generating first preliminary data for generation of the input data and second preliminary data for generation of the label data by combining the plurality of pieces of data; and generating the input data and the label data by transforming the first preliminary data and the second preliminary data into an image domain, and wherein generating the first preliminary data for the generation of the input data and the second preliminary data for the generation of the label data by combining the plurality of pieces of data comprises generating the first preliminary data and the second preliminary data through linear combination that adjusts a noise ratio between the plurality of pieces of data.

2. The method of claim 1, wherein the metadata includes at least one of a number of excitations (NEX), an acceleration factor, a parallel imaging technique applied to the k-space data, and a resolution.

3. The method of claim 1, wherein noise of the second preliminary data includes dependent noise that has a correlation with noise of the first preliminary data and independent noise that has no correlation with the noise of the first preliminary data.

4. The method of claim 3, wherein in the noise of the second preliminary data, each of the dependent noise and the independent noise is determined by a coefficient used for linear combination between the plurality of pieces of data.

5. The method of claim 1, wherein generating the input data and the label data by transforming the first preliminary data and the second preliminary data into the image domain comprises generating the input data and the label data based on Fourier transform for the first preliminary data and the second preliminary data.

6. The method of claim 1, wherein generating the input data and the label data by transforming the first preliminary data and the second preliminary data into the image domain comprises generating the input data and the label data by inputting the first preliminary data and the second preliminary data to a neural network model.

7. The method of claim 1, wherein generating the input data and the label data for the training of the deep learning model by combining the plurality of pieces of different data separated from the k-space data comprises adjusting a resolution of the first preliminary data.

8. The method of claim 7, wherein adjusting the resolution of the first preliminary data comprises adjusting at least one of a basic resolution and phase resolution of the first preliminary data so that the resolution of the first preliminary data has a value smaller than or equal to a resolution of the second preliminary data.

9. A non-transitory computer-readable storage medium having computer program instructions stored thereon for performing operations of processing medical data for training of a deep learning model when the computer program instructions are executed on at least one processor, wherein the operations comprise operations of:

separating k-space data into a plurality of pieces of different data by taking into consideration characteristics of metadata of the k-space data; and generating input data and label data for training of a deep learning model by combining the plurality of pieces of different data separated from the k-space data, wherein generating the input data and the label data for the training of the deep learning model by combining the plurality of pieces of different data separated from the k-space data comprises:

generating first preliminary data for generation of the input data and second preliminary data for generation of the label data by combining the plurality of pieces of data; and generating the input data and the label data by transforming the first preliminary data and the second preliminary data into an image domain, and wherein generating the first preliminary data for the generation of the input data and the second preliminary data for the generation of the label data by combining the plurality of pieces of data comprises generating the first preliminary data and the second preliminary data through linear combination that adjusts a noise ratio between the plurality of pieces of data.

10. A computing device for processing medical data for training of a deep learning model, the computing device comprising:

a processor including at least one core;

memory including program code executable on the processor; and a network unit configured to acquire k-space data and meta data of the k-space data;

wherein the processor separates k-space data into a plurality of pieces of different data by taking into consideration characteristics of metadata of the k-space data, and generates input data and label data for training of a deep learning model by combining the plurality of pieces of different data separated from the k-space data, wherein the processor, in generating the input data and the label data, generates first preliminary data for generation of the input data and second preliminary data for generation of the label data by combining the plurality of pieces of data, generates the input data and the label data by transforming the first preliminary data and the second preliminary data into an image domain, and generates the first preliminary data and the second preliminary data through linear combination that adjusts a noise ratio between the plurality of pieces of data.

* * * * *